United States Patent
Nasser-Ghodsi et al.

(10) Patent No.: US 7,635,842 B2
(45) Date of Patent: Dec. 22, 2009

(54) METHOD AND INSTRUMENT FOR CHEMICAL DEFECT CHARACTERIZATION IN HIGH VACUUM

(75) Inventors: Mehran Nasser-Ghodsi, Halmilton, MA (US); Ming Lun Yu, Fremont, CA (US); Stuart Friedman, Palo Alto, CA (US); Gabor Toth, San Jose, CA (US)

(73) Assignee: KLA-Tencor Corporation, San Jose, CA (US)

( * ) Notice: Subject to any disclaimer, the term of this patent is extended or adjusted under 35 U.S.C. 154(b) by 119 days.

(21) Appl. No.: 12/032,526

(22) Filed: Feb. 15, 2008

(65) Prior Publication Data

US 2008/0197277 A1  Aug. 21, 2008

Related U.S. Application Data

(60) Provisional application No. 60/890,512, filed on Feb. 19, 2007.

(51) Int. Cl.
*H01J 49/08* (2006.01)
*G01N 23/227* (2006.01)
*G01N 23/22* (2006.01)

(52) U.S. Cl. .............. 250/306; 250/307; 250/310; 250/305; 250/492.2; 250/492.3

(58) Field of Classification Search ............ 250/306, 250/307, 310, 305, 492.2, 492.3
See application file for complete search history.

(56) References Cited

U.S. PATENT DOCUMENTS

| | | | |
|---|---|---|---|
| 6,294,469 B1 | 9/2001 | Kulkarni et al. | |
| 6,661,515 B2 | 12/2003 | Worster et al. | |
| 6,753,261 B1 | 6/2004 | Phan et al. | |
| 7,097,708 B2 * | 8/2006 | Clark et al. | 117/94 |
| 2007/0194251 A1 * | 8/2007 | Ward et al. | 250/492.21 |

FOREIGN PATENT DOCUMENTS

WO  WO 99/35668  1/1999

OTHER PUBLICATIONS

U.S. Appl. No. 11/622,625 entitled "Structural Modification Using Electron Beam Activated Chenial Etch" filed Jan. 12, 2007.
U.S. Appl. No. 60/890,512 entitled "Method and Instrument for Chemical Defect Characteriszation in High Vacuum" filed Feb. 19, 2007.
M. Jacka et al., "A fast, parallel acquisition, electron energy analyzer: The hyperbolic field analyzer", Review of Scientific Instrument, vol. 70, No. 5, May 1999. pp. 2282-2287.
International Search Report and Written Opinion of the International Searching Authority dated Jul. 18, 2008—International Patent Application No. PCT/ US08/54155.

\* cited by examiner

*Primary Examiner*—Nikita Wells
(74) *Attorney, Agent, or Firm*—Joshua D. Isenberg; JDI Patent

(57) ABSTRACT

A method and the instrument for characterization of the defects on a surface with Auger electron spectroscopy in a high vacuum environment are disclosed. Defects on the surface of a sample may be characterized with Auger electron spectroscopy in a high vacuum environment.

24 Claims, 4 Drawing Sheets

METHOD AND INSTRUMENT FOR CHEMICAL DEFECT CHARACTERIZATION IN HIGH VACUUM

CLAIM OF PRIORITY

This application claims the benefit of priority of commonly-assigned U.S. Provisional Patent Application No. 60/890,512 filed Feb. 19, 2007, the entire contents of which are incorporated herein by reference.

FIELD OF THE INVENTION

This invention generally relates to an electron energy analyzing system and more particularly to such a system for Auger electron spectroscopy in high vacuum.

BACKGROUND OF THE INVENTION

Over the past few years, the demand for ever cheaper and lighter weight portable electronic devices has led to a growing need to manufacture durable, lightweight, and low cost electronic circuits including high density memory chips. The increasing complexity of electronic devices, and integrated circuits, coupled with the decreasing size of individual circuit elements, places ever more stringent demands on fabrication processes, particularly with respect to the resolution and accuracy of the fabrication patterns. The ability to fabricate on a nanometer scale guarantees a continuation in miniaturization of functional devices. Micro-fabrication techniques can produce structures having features on the order of nanometers. Micro-fabrication is used in a wide variety of applications, such as the manufacturing of integrated circuits (i.e. semiconductor processing), biotechnology, optical technology, mechanical systems, and micro-electro-mechanical systems ("MEMS").

Micro-fabrication is typically a multi-step process involving the patterned deposition or removal of material from one or more layers that make up a finished device. Micro-fabrication is sensitive to the presence of contaminant particles. In micro-fabrication it is common to inspect a substrate for the presence of contaminants between process steps. As the size of micro-fabricated features decreases, smaller and smaller contaminant particles and films can affect device yield. A number of tools have been developed for detecting contaminant particles. Inspection tools, such as a scanning electron microscope (SEM) are commonly used to inspect a partially fabricated device or wafer containing multiple devices for defects. For certain cases, it may be sufficient to image the defects, e.g., with the SEM and analyze the image to characterize the defects. But for many cases, once defects have been detected it is important to chemically characterize them Instrumentation for use in spectroscopy of charged particles for chemical analysis makes use of electrons or ions which are emitted from a substance after being bombarded or irradiated with electrons or ions from a source such as an electron gun. Energy Dispersive X-ray analysis (EDX) is a technique in which an electron beam strikes the surface of a conducting sample. The energy of the beam is typically in the range 5-20 kilo electro-volts (keV). This causes X-rays to be emitted from the point the material. The energy of the X-rays emitted depends on the material under examination. For EDX, the X-rays are generated in a region about 2 microns in depth. For sufficiently large defects, EDX may have adequate sensitivity and spatial resolution. Unfortunately, for very small defects, e.g., less than about 50 nm in size, EDX does not have the sensitivity to chemically characterize them.

Another charged particle spectroscopy technique is known as Auger electron spectroscopy. In this technique, a target sample material is placed in an ultra high vacuum (UHV) environment, typically about $10^{-10}$ Torr to $10^{-9}$ Torr, and upon being bombarded with electrons from some source, such as an electron gun, the sample gives off a variety of emissions. Among these are X-rays, secondary electrons, and reflected primary electrons from the source. The emissions include Auger electrons (a particular class of secondary electrons) in the manner which is well known in the literature. Auger electron spectroscopy is a surface analytical technique because the energies of the electrons emitted are typically in the range of 50 eV to 3 keV, and at this energy they cannot escape from more than a few nanometers deep in the surface (of course, the higher the energy, the thicker the layer from which they can escape). For Auger spectroscopy to be conducted the sample chamber and spectrometer must be maintained at Ultra High Vacuum (UHV), as any gasses present will form a thin 'adsorbed gas layer' on the surface of the sample attenuating the Auger electron signals from the sample. However, the design complexity of UHV systems and slower operational cycle prevents rapid analysis of defects in production-scale substrate processing, which tend to operate at high vacuum, e.g., about $10^{-7}$ to about $10^{-6}$ torr.

It is within this context that embodiments of the present invention arise.

BRIEF DESCRIPTION OF THE DRAWINGS

Objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Introduction

Defects in a substrate that can be detected by scanning electron microscope (SEM) but are too small to be imaged with the SEM may be chemically characterized using a charged particle spectroscopy technique such as Auger electron spectroscopy. In the art of Auger electron spectroscopy, the electron energy analyzers operate by injecting the diverging electrons into an electric field using a few simply shaped electrodes. Auger electrons of a particular energy injected from the sample into the electric field are deflected by the field toward a common focus. Electrons of a predetermined energy are thereby brought to a focus. By positioning a collector apparatus at this focus, electrons of a predetermined energy may be selected and detected. By sweeping the voltage impressed across the electrodes through a range of values, and detecting electrons as a function of these applied potentials such electrons as are collected, the energy spectrum of the injected electrons may be plotted and determined.

Electron spectrometers used for Auger electron spectroscopy and similar techniques, such as ultraviolet photon spectroscopy (UPS) or X-ray photon spectroscopy (XPS), conventionally use a cylindrical mirror analyzer (CMA) to obtain a secondary electron energy spectrum. A CMA uses the electric field between two concentric metal cylinders to select secondary electrons according to energy. Only electrons with the right energy will make it through the field region between the cylinders and strike a detector. A spectrum is obtained by varying the voltage applied between the cylinders and measuring the electron signal at the detector as a function of energy. Unfortunately, scanning the voltage to obtain a signal must often be done quite slowly, e.g., on the order of several minutes. Consequently, Auger spectrometers have been operated in ultra-high vacuum (UHV) environments (about $10^{-9}$ Torr to $10^{-10}$ Torr) so that the spectrum can be obtained before a significant build-up of adsorbates (e.g., about 1 to 3 monolayers) can occur. Although UHV systems are commonly used for analytical tools in research and failure analysis, it is expensive and time consuming to implement UHV systems in a semiconductor wafer production environment. Consequently, charged particle spectroscopy techniques, such as Auger, that require a UHV environment are not used in production-scale substrate processing systems such as semiconductor wafer fabs.

Figure 1:
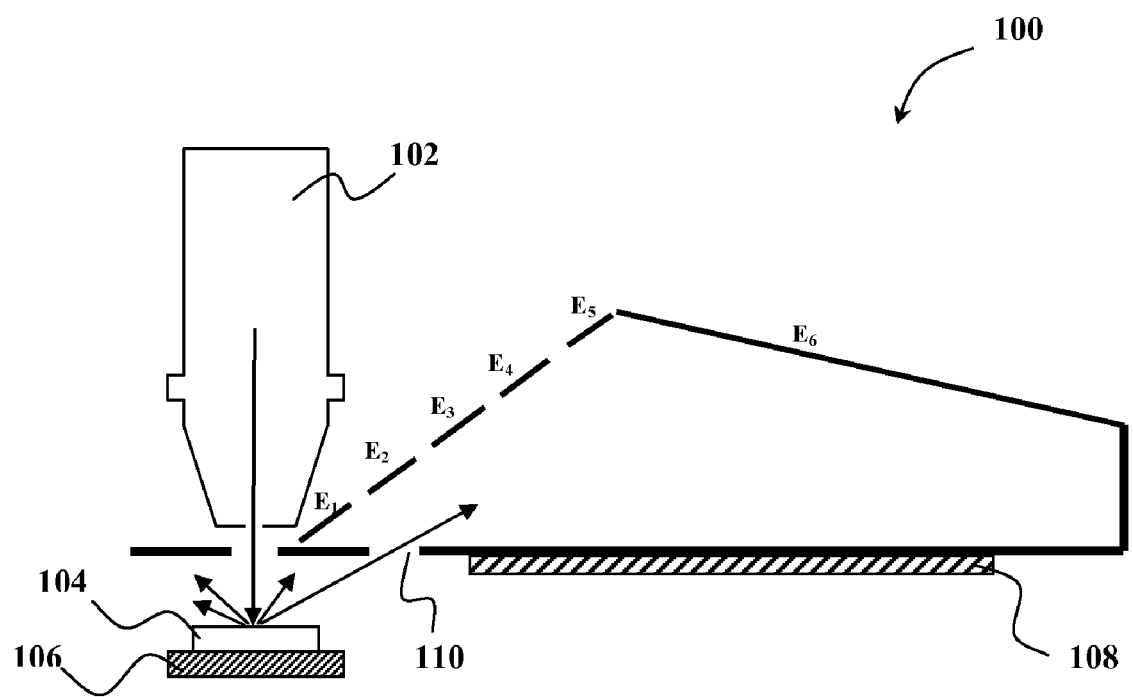
FIG. 1 is a schematic diagram illustrating a prototype hyperbolic field analyzer of a type that may be used in conjunction with embodiments of the present invention.

FIG. 1 is a schematic diagram illustrating a prototype hyperbolic field analyzer 100, which may be used in embodiments of the present invention. Primary radiation from an source 102 (e.g., an electron beam column in the case of Auger, an ultraviolet source in the case of UPS or an X-ray source in the case of XPS) bombards the surface of a sample 104 placed on a sample holder 106. Interaction between the primary radiation and the sample 104 causes secondary electrons to be emitted. Some of the secondary electrons enter the analyzer 100 through an aperture 110, where they are subjected to a substantially hyperbolic electric field, which may be approximated with a small number of electrodes $E_1$ to $E_6$. As shown in FIG. 1, the electrodes $E_1$ to $E_5$ are arranged in a plane which is inclined to the axis of the detector 108, and the electrode $E_6$ is similarly inclined, but in an opposite direction. Each electrode is connected via a set of adjustable voltage dividers to a single power supply, allowing on-line control of the shape of the field. More details about hyperbolic field and hyperbolic field analyzer prototype can be found in International Publication No. WO 99/35668 entitled "Charged Particle Analysers" to Prutton et al., filed Jan. 12, 1999, and in "A fast, parallel acquisition, electron energy analyzer: The hyperbolic field analyzer" by M. Jacka et al. in *Review of Scientific Instruments* Vol. 70, No. 5, May 1999, which are incorporated herein by reference.

An important feature of the electron energy analyzer 100 is the ability to detect electrons over a large range of energy in parallel over an energy range associated with Auger electrons (e.g., about 50 eV to about 2050 eV). In general terms, the substantially hyperbolic field deflects the secondary electrons to impinge upon a detector 108 at different locations depending on secondary electron energy. By way of example, the detector 108 may include a microchannel plate and a phosphor screen to detect secondary electrons of different energies at different locations. The microchannel plate detects electron signals at multiple locations in parallel and produces a separate signal for each location or "channel". Because the signal at each location depends on the energy of electrons that impinge on the detector at that location, the analyzer 100 can obtain a secondary electron energy spectrum in a very short period of time, e.g., on the order of about 1 or 2 seconds. It turns out that this is sufficiently fast that an Auger spectrum could be obtained in a high vacuum environment (about $10^{-6}$ to $10^{-7}$ torr) before more than about 1 to 3 monolayers of adsorbates from background gas would build up on the sample 104. Consequently, the analyzer 100 could be used to chemically characterize defects that are too small to image with an SEM or other imaging technique.

Those skilled in the substrate processing arts have long recognized the need for chemical characterization of very small defects. Unfortunately, many of the suggested defect characterization techniques do not provide chemical specific information. For example, transmission Electron Microscopy (TEM) with energy dispersion X-ray (EDX) or energy-loss spectroscopy, has been suggested for characterization of very small defects. Unfortunately, this technique does not provide chemical specific information and further requires a very thin sample for an electron beam to pass through. Scanning tunneling microscopy (STM) in conjunction with I-V curve or scanning near field optical spectroscopy has also been suggested. Although the sample need be thin, the results do not provide chemical specific information.

It is noted that certain pre-existing notions of those in the charged particle spectroscopy and substrate processing arts would weigh against using the analyzer 100 for chemical characterization of defects in a production-scale processing environment. Specifically, those skilled in the charged particle spectroscopy and substrate processing arts associate techniques like Auger spectroscopy with ultra-high vacuum environments, but not high vacuum environments. Thus, those skilled in the substrate processing arts would not expect Auger spectroscopy to work in a production-scale substrate processing environment.

Figure 2:
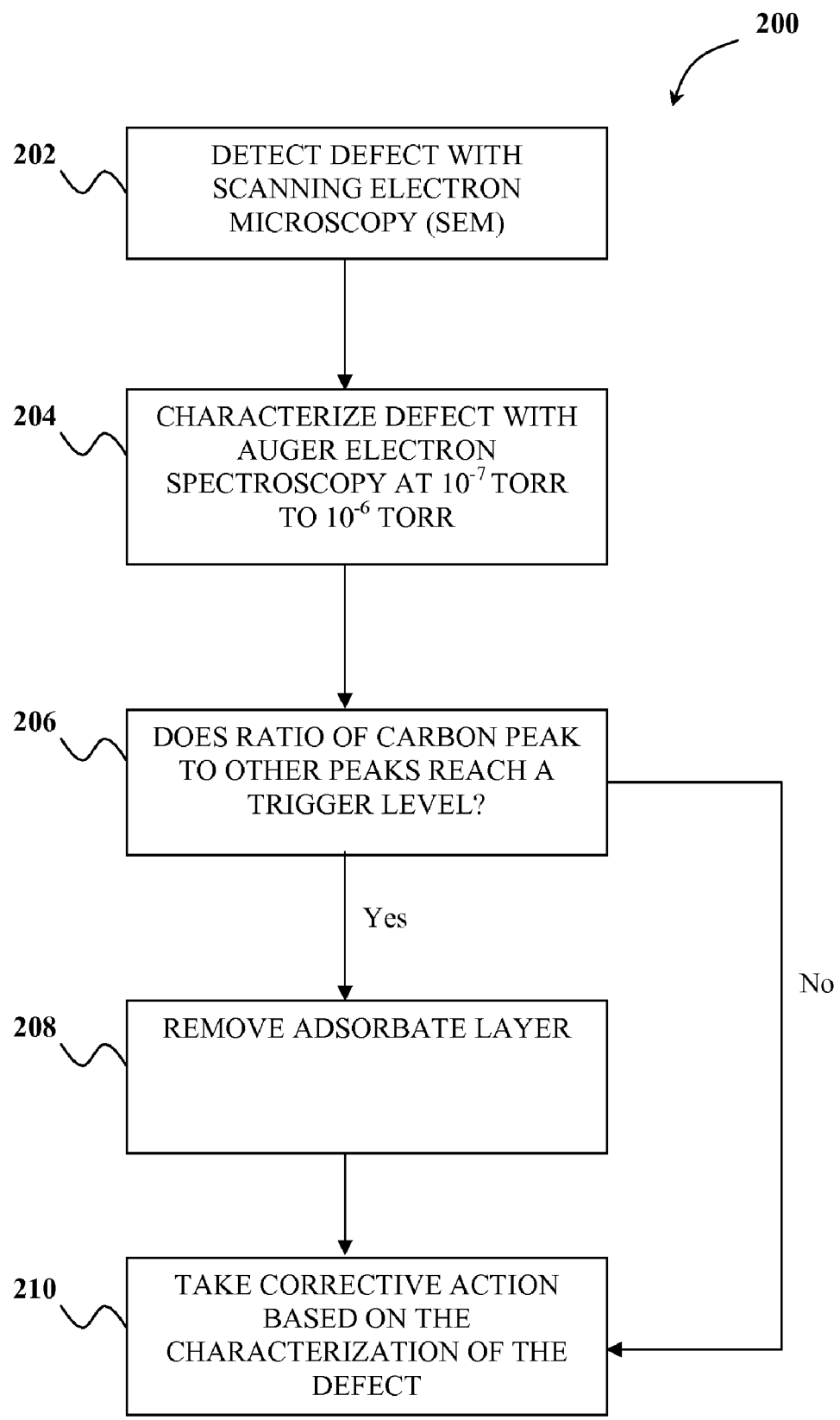
FIG. 2 is a flow diagram illustrating a method of characterization of a defect on a surface of a sample with Auger electron spectroscopy at high vacuum according to an embodiment of the present invention.

FIG. 2 depicts a flow diagram illustrating a method 200 for characterization the defect on the surface of a sample, such as a reticle or semiconductor wafer. In general, the method involves detecting the defect on the surface of the sample as indicated at 202. Typically, the defect is detected with Scanning Electron Microscopy (SEM). The detected defect is then characterized with Auger Electron Spectroscopy (AES) in a high vacuum environment at $10^{-7}$ Torr to $10^{-6}$ Torr as indicated in 204.

As described above, the electrons from an electron beam, which can be the electron beam from the scanning electron microscope, are bombarded on the defects and an Auger spectrum is captured. There are gasses present in the high vacuum environment and will absorb and scatter the very low energy Auger electrons as well as forming a thin 'adsorbed gas layer' on the surface of the sample, which degrades analytical performance. Such gases often contain carbon and/or hydrocarbons. Consequently, the carbon peak can be a prominent peak in an Auger spectrum.

Typically, in a high vacuum environment at 10-7 Torr to 10-6 Torr, about one monolayer of the adsorbates will build up on the surface of the sample in about one to few seconds. A thickness of one monolayer is about 3 Å. Therefore, an Auger spectrum should be captured in a time less than or equal to a time to build up about one monolayer of adsorbates, i.e., at about 1 second. Auger attenuation length usually is about several nm, i.e., about 10-20 Å. In order to capture useful Auger spectra at the high vacuum, the adsorbates layer may have to be removed since there is noticeable reduction in signal with each monolayer of the adsorbates. Since the carbon peak is often associated with adsorbates it can reasonably be expected that the signal strength of this peak will tend to increase with time, while other peaks associated with the material of the sample can be expected to decrease.

A ratio of the Carbon peak to other peaks in the Auger spectra may be monitored with the carbon peak being used as a reference for the other peaks as indicated in 206. When the ratio of the Carbon peak to other peaks reaches a trigger level, the adsorbates layer may be cleaned as indicated in 208. There are several techniques can be used to clean the adsorbates layer, which include, but are not limited to, ion sputtering (e.g., with Argon ions) or electron beam activated chemical etching (EBACE). Electron beam activated chemical etching (EBACE) generally includes introducing an etchant, typically in the form of a gas or vapor, to the sample in conjunction with the electron beam. More details on the EBACE can be found in U.S. application Ser. No. 11/622,625 entitled "Structural Modification Using Electron Beam Activated Chemical Etch" to Mehran-Nasser Ghodsi et al., which is incorporated herein by reference.

The secondary electrons emitted from the defect and/or regions of the sample proximate the defect are monitored to keep the electron beam on the defect to compensate for drift. The secondary electron can be monitored with, but not limited to, scanning electron microscopy. After the defect is characterized with secondary electron spectroscopy (e.g., Auger spectroscopy, UPS or XPS), corrective actions may be taken as indicated in 210. Examples of corrective action include, e.g., removing the defect from the sample if the defect is minor or discarding the wafer if the defect is major.

Figure 3A:
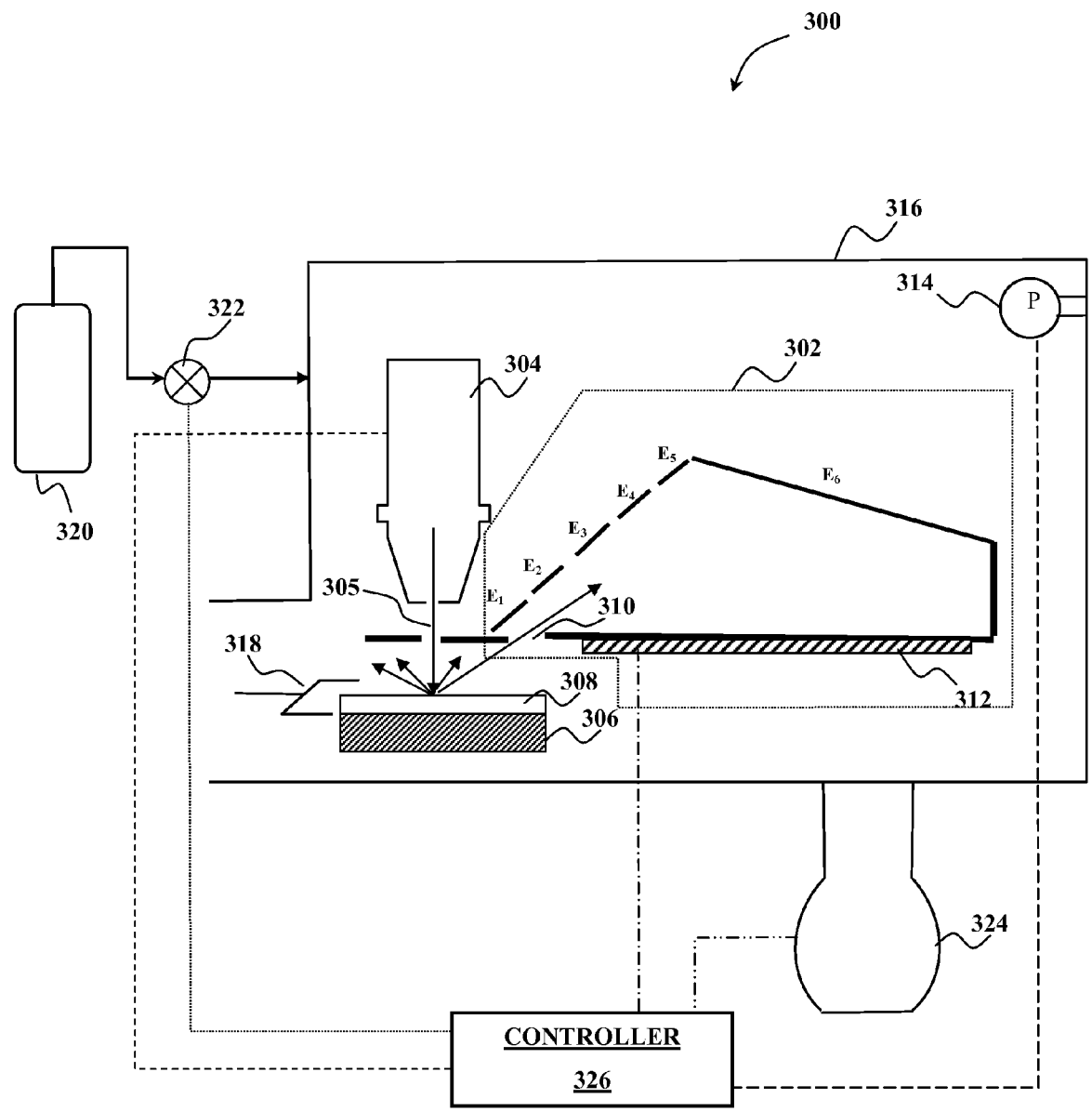
FIG. 3A is a schematic diagram of an instrument for characterization of defects on a surface of a sample according to an embodiment of the present invention.

FIG. 3A is a schematic diagrams illustrating an instrument 300 for characterization of small defects on a surface of a sample in a production-scale substrate processing system. By way of example, the instrument is adapted to characterize defects on samples such as semiconductor wafers or reticles having a diameter equal or larger than 100 mm. The sample may have a diameter equal or larger than 200 mm or greater than or equal to 300 mm. As shown in FIG. 3A, the instrument 300 includes an electron energy analyzer 302 of the type depicted in FIG. 1, which includes, but not limited to, six electrodes $E_1$ to $E_6$, each of which is connected via a set of adjustable voltage dividers to a single power supply, which are not shown, allowing on-line control of the shape of the hyperbolic field. The electron energy analyzer 302 also includes a detector 312 containing a microchannel plate and a phosphor screen. The instrument 300 may also include a scanning electron microscope 304 for detecting defects on the surface of a sample 308, which is placed on a susceptor 306, and also providing primary radiation in the form of an electron beam 305 to excite emission of secondary electrons from the defect.

Secondary electrons (e.g., Auger electrons) emitted from the defect enter the analyzer 302 through an aperture 310. The electron energy analyzer 302 capably captures an Auger spectrum in a time equal or less than a time to build up one monolayer of adsorbates from the high vacuum environment, i.e. at $10^{-7}$ Torr to $10^{-6}$ Torr, typically about 1 second. The scanning electron microscope 304 may also be used to monitor the secondary electrons emitted from the defect and/or the regions of the sample 308 proximate the defect to keep the electron beam centered on the defect to compensate for drift. For example, once a contrast in an image containing the defect has been established the primary electron beam may be kept centered on the defect by changing the substrate location or primary electron beam landing location in response to changes in contrast.

The holder 306 may be a susceptor, such as a chuck, that holds the sample 308 during operation of the instrument 300. The holder 306 is preferably sized to receive and/or hold substrates 100 mm in diameter or larger, 200 mm in diameter or larger or 300 mm in diameter or larger. The electron energy analyzer 302, the scanning electron spectroscope 304, the sample 308 and the holder 306 are housed in a vacuum chamber 316, which is maintain at a high vacuum of $10^{-7}$ Torr to $10^{-6}$ Torr. A vacuum system is coupled to the vacuum chamber 316, which is configured to maintain a high vacuum in the vacuum chamber 316 during capture of the Auger spectrum. The vacuum system typically includes a vacuum pump 324 and fittings, which are not shown. The vacuum pump 324 could be an ion pump, a diffusion pump, or a turbomolecular pump, which is backed up by a rotary pump. Fittings may be sealed with gaskets or O-rings made of a high-vacuum compatible elastomer such as Viton® or other similar synthetic rubber. Viton® is a register trademark of Dupont Performance Elastomers LLC of Wilmington Del. A pressure gauge 314 is adapted to monitor the pressure of the vacuum chamber 316. The pressure gauge 314 could be capacitance manometer, ionization gauge or thermocouple gauge.

The instrument 300 also includes a gas source 320 for cleaning the adsorbates in the vacuum chamber 316. The gas source 320 could be an inert gas source (e.g., a source of Argon) used in association with an ion source (e.g., an ion beam gun) or a source of an etchant used in EBACE. The gas from the gas source 320 is introduced into the vacuum chamber 316 through a valve 322. The instrument 300 also includes a controller 326 coupled to the scanning electron microscope 304 to control the focus of the electron beam 305 on the defect. The controller 326 is also coupled to the detector 312 to monitor the ratio of the carbon peak to other peaks. In addition, the controller 326 may be coupled to the gas valve 322 to control the gas flow from the gas source 320 to the vacuum chamber 316 for cleaning the adsorbates when the ratio of the carbon peak to other peaks reaches the trigger level. The controller 326 may also be coupled to the pressure gauge 314 and the vacuum pump 324 to maintain appropriate pressure in the vacuum chamber 316.

Figure 3B:
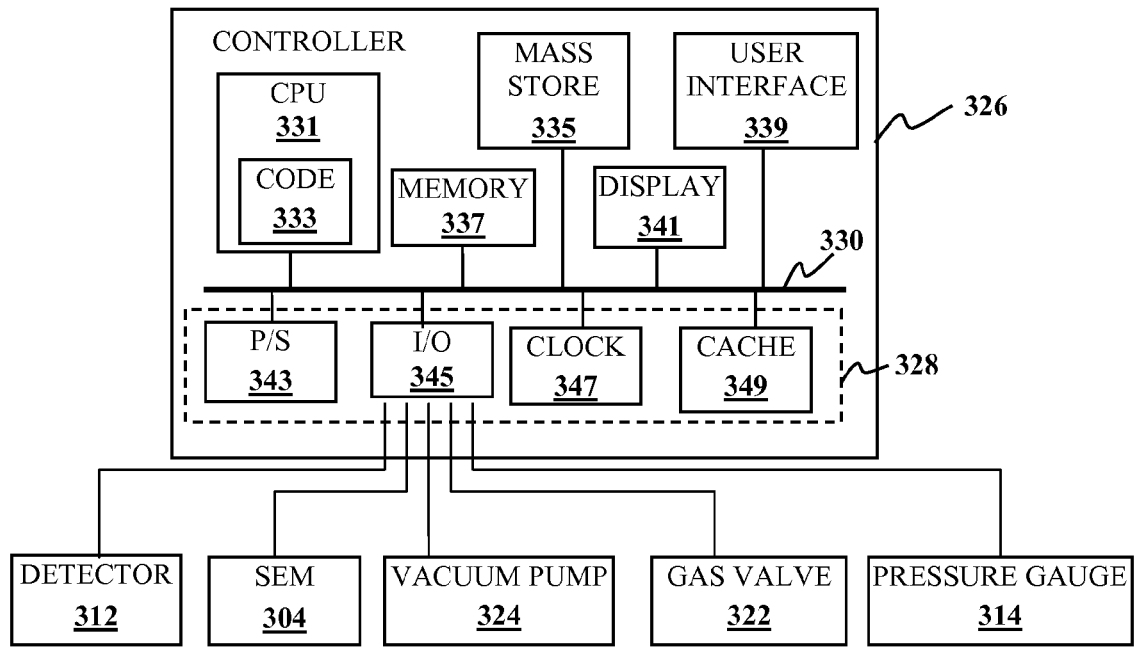
FIG. 3B is a block diagram illustrating a controller of the instrument described in FIG. 3A.

The controller 326 may be a self-contained microcontroller. Alternatively, as shown in FIG. 3B, the controller 326 may be a general purpose computer configured to include a central processor unit (CPU) 331, memory 337 (e.g., RAM, DRAM, ROM, and the like) and well-known support circuits 328 such as power supplies 343, input/output (I/O) functions 345, clock 347, cache 349, and the like, coupled to a control system bus 330. The memory 337 may contain instructions that the CPU 331 executes to facilitate the performance of the instrument 300. The instructions in the memory 331 may be in the form of a program code 333. The code 333 may control, e.g., the focus of the electron beam on the defect, control the gas flow from the gas source 320 to the vacuum chamber 316 for cleaning the adsorbates and control the pressure in the vacuum chamber 316.

The code 333 may conform to any one of a number of different programming languages such as Assembly, C++, JAVA or a number of other languages. The controller 326 may also include an optional mass storage device, 335, e.g., CD-ROM hard disk and/or removable storage, flash memory, and the like, which may be coupled to the control system bus 330. The controller 326 may optionally include a user interface 339, such as a keyboard, mouse, or light pen, coupled to the CPU 331 to provide for the receipt of inputs from an operator (not shown). The controller 326 may also optionally include a display unit 341 to display images generated by the detector 312 and/or to provide information to the operator in the form of graphical displays and/or alphanumeric characters under control of the processor unit 331. The display unit 341 may be, e.g., a cathode ray tube (CRT) or flat screen monitor.

Figure 3C:
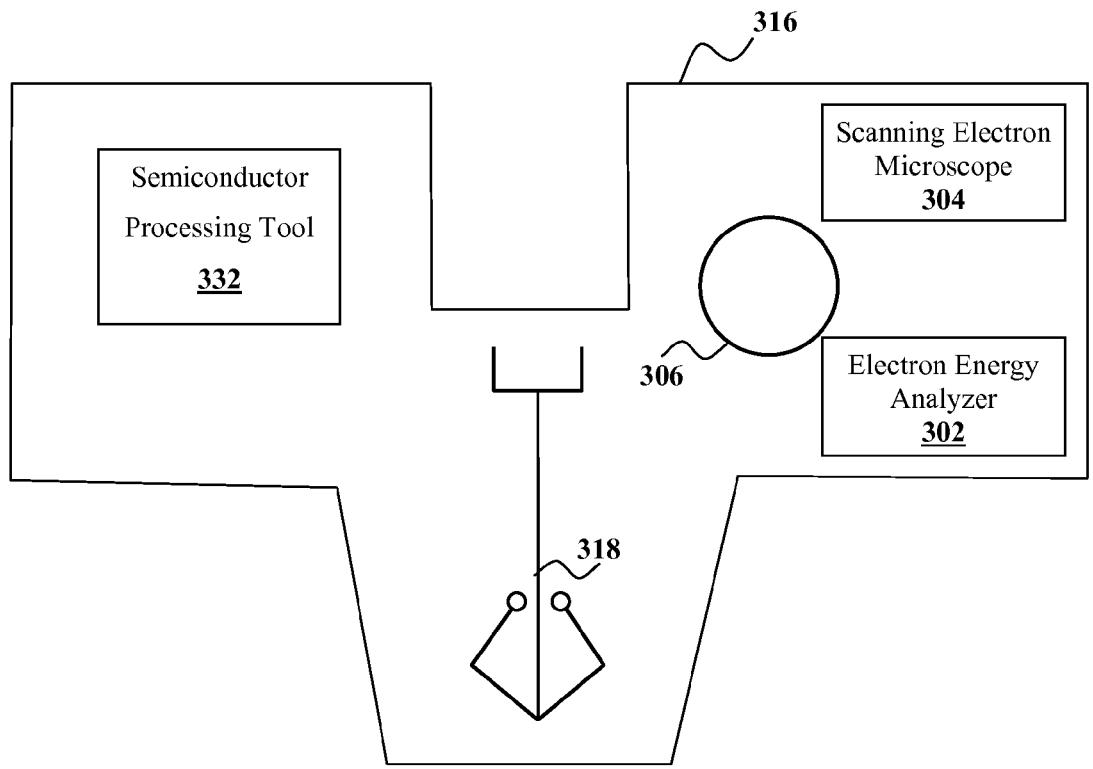
FIG. 3C is a diagram showing the vacuum chamber of the instrument of the present invention coupled to other semiconductor processing tools.

As shown in FIG. 3C, the vacuum chamber 316 of the instrument 300 may be adapted to couple to one or more semiconductor processing tools 332. The processing tool 332 could be, but not limited to, cluster tools, inspection tools or metrology tools. Substrates, such as semiconductor wafers and/or reticles, may be transferred between the holder 306 and other processing tools, e.g., using a robot arm 318.

Embodiments of the present invention allow for chemical characterization of defects that are too small to be characterized by imaging. Such defects may be chemically characterized in a production-scale substrate processing environment at pressures ranging from about $10^{-7}$ torr to about $10^{-7}$ torr.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for characterizing a defect on a surface of a sample, comprising:
   detecting the defect; and
   characterizing the defect with Auger electron spectroscopy in a high vacuum environment by capturing an Auger spectrum in a time that is less than or equal to a time to build up about one monolayer of adsorbates from the high vacuum environment.

2. The method of claim 1, wherein the step of detecting the defect is performed using Scanning Electron Microscopy (SEM).

3. The method of claim 1, wherein the step of characterizing the defect comprises:
   bombarding the defect with electrons from an electron beam column of a scanning electron microscope.

4. The method of claim 3 after the step of characterizing the defect further comprising cleaning the adsorbates from the sample when a ratio of a reference peak to other peaks in the secondary electron spectrum reaches a trigger level.

5. The method of claim 4 wherein the step of cleaning the adsorbates includes removing the adsorbates by sputtering with ions.

6. The method of claim 4 wherein the step of cleaning the adsorbates is performed using electron beam activated chemical etching (EBACE).

7. The method of claim 6 wherein the electron beam activated chemical etching (EBACE) comprises introducing an etchant in the form of a gas or vapor to the sample in conjunction with exposing the surface of the sample to an electron beam.

8. The method of claim 3 after the step of characterizing the defect further comprising monitoring secondary electrons emitted from the defect and or regions of the sample proximate the defect to keep the electron beam on the defect to compensate for drift of the electron beam.

9. The method of claim 8 wherein the step of monitoring the secondary electrons is performed using scanning electron microscopy.

10. The method of claim 1 after the step of characterizing the defect further comprising taking corrective action based on the characterization of the defect.

11. The method of claim 1 wherein the defect is smaller than about 50 nanometers in size.

12. An instrument for characterizing a defect on a surface of a sample comprising:
    a primary electron source, configured to direct primary radiation to a measurement location on the sample;
    an electron energy analyzer configured to capture a spectrum of Auger secondary electrons from the measurement location in a time that is less than or equal to a time to build up about one monolayer of adsorbates from a high vacuum environment;
    a susceptor for holding a semiconductor wafer having a diameter equal or larger than 100 mm;
    a vacuum chamber for housing the electron source, the electron energy analyzer and the susceptor, wherein the vacuum chamber is configured to maintain a high vacuum;
    a vacuum system coupled to the vacuum chamber, wherein the vacuum system is configured to maintain a high vacuum in the chamber during the capture of the secondary electron spectrum,
    wherein the vacuum chamber is adapted to couple to one or more semiconductor processing tools.

13. The instrument of claim 12 wherein the vacuum system comprising a vacuum pump.

14. The instrument of claim 13, wherein the vacuum pump is a diffusion pump or a turbo-molecular pump.

15. The instrument of claim 12 wherein the vacuum system further comprising fittings.

16. The instrument of claim 15 wherein the fittings include elastomer gaskets or O-rings.

17. The instrument of claim 12 wherein the semiconductor processing tools are cluster tools, inspection tools or metrology tools.

18. The instrument of claim 12 wherein the primary radiation source is an electron beam column of a scanning electron microscope.

19. The instrument of claim 12 further comprising an ion source adapted for removing adsorbates from the high vacuum environment from the measurement location.

20. The instrument of claim 12 further comprising a controller configured to control a pressure within vacuum of the vacuum chamber.

21. The instrument of claim 12, further comprising a controller configured to control a focus of the electron beam on the defect.

22. The instrument of claim 12 further comprising a gas source coupled to the vacuum chamber.

23. The instrument of claim 22, further comprising a controller configured to control the gas flow for cleaning the adsorbates.

24. The instrument of claim 22, wherein the gas source comprises an etchant source.

* * * * *